US00PP24511P3

(12) United States Plant Patent

Mezzetti et al.

(10) Patent No.: US PP24,511 P3

(45) Date of Patent: Jun. 3, 2014

(54) STRAWBERRY PLANT NAMED 'CRISTINA'

(50) Latin Name: *Fragaria×ananassa*
Varietal Denomination: Cristina

(75) Inventors: Bruno Mezzetti, Ancona (IT); Franco Capocasa, Massignano-Ascoli Piceno (IT)

(73) Assignee: Hargreaves Plants Limited, Spalding, Lincolnshire (GB)

( * ) Notice: Subject to any disclaimer, the term of this patent is extended or adjusted under 35 U.S.C. 154(b) by 87 days.

(21) Appl. No.: 13/506,965

(22) Filed: May 29, 2012

(65) Prior Publication Data

US 2012/0311749 P1 Dec. 6, 2012

(30) Foreign Application Priority Data

May 30, 2011 (QZ) ..... PBR 20111274

(51) Int. Cl.
*A01H 5/00* (2006.01)

(52) U.S. Cl.
USPC ..... Plt./208; Plt./209

(58) Field of Classification Search
USPC ..... Plt./208, 209
See application file for complete search history.

*Primary Examiner* — Susan McCormick Ewoldt
(74) *Attorney, Agent, or Firm* — Jondle Plant Sciences division of Swanson & Bratschun, L.L.C.

(57) ABSTRACT

A new and distinct variety of strawberry plant named 'Cristina' particularly characterized by high adaptability to non-fumigated soil, very late ripening, very large fruit with good taste, and high productivity, is disclosed.

2 Drawing Sheets

Genus and species: *Fragaria×ananassa.*
Variety denomination: 'Cristina'.

CROSS REFERENCE TO RELATED APPLICATIONS

This application claims the benefit of priority from EU Community Plant Variety Rights (CPVR) application no. 20111274, filed May 30, 2011, which is incorporated herein by reference in its entirety.

BACKGROUND OF THE NEW PLANT

The present invention relates to a new and distinct June-bearing strawberry variety designated 'Cristina' and botanically known as *Fragaria×ananassa*. This new strawberry variety was discovered in Cesena, Italy in 2001 and originated from a cross between the female parent, selection 'CN95,602, 8' (unpatented, selection of National Breeding Programme Strawberry Project—Italy) and the male parent, selection 'CN95,419,4' (unpatented, selection of National Breeding Programme Strawberry Project—Italy). 'Cristina' was first fruited in Ancona, Italy in 2003, where it was selected and originally designated AN01,211,51.

The present invention has been found to retain its distinctive characteristics through successive asexual propagations via stolons and tissue culture.

Plant Breeder's Rights for this variety have been applied for in Europe on May 30, 2011 having CPVR application no. 20111274. 'Cristina' has not been made publicly available or sold more than one year prior to the filing date of this application.

SUMMARY OF THE INVENTION

The following are the most outstanding and distinguishing characteristics of this new cultivar when grown under normal horticultural practices in Ancona, Italy.

1. High adaptability to non-fumigated soil;
2. Very late ripening;
3. Very large fruit with good taste; and
4. High productivity.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from ten-month-old plants.

DESCRIPTION OF THE NEW VARIETY

Figure 1:
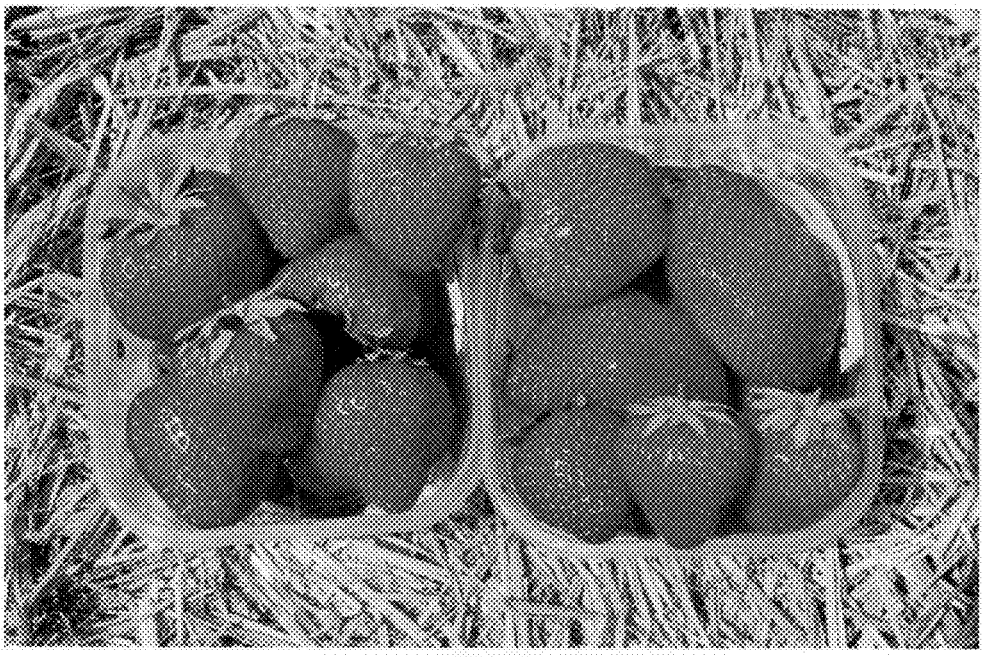
FIG. 1 shows the whole fruit.
Figure 2:
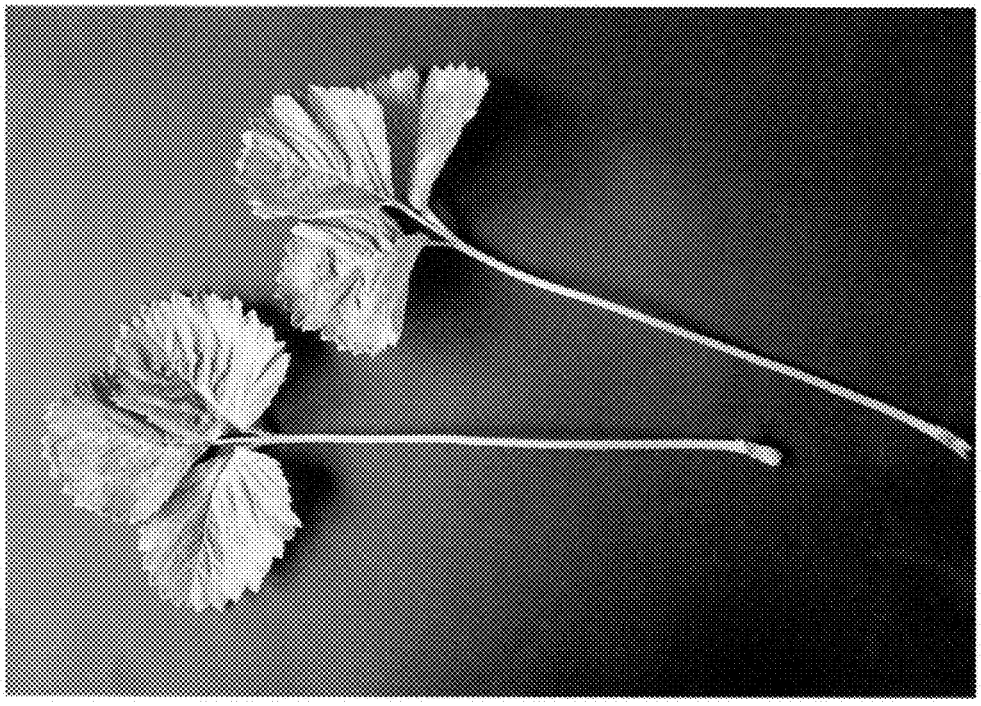
FIG. 2 shows upper and lower surfaces of the leaves of the plant with three leaflets.
Figure 3:
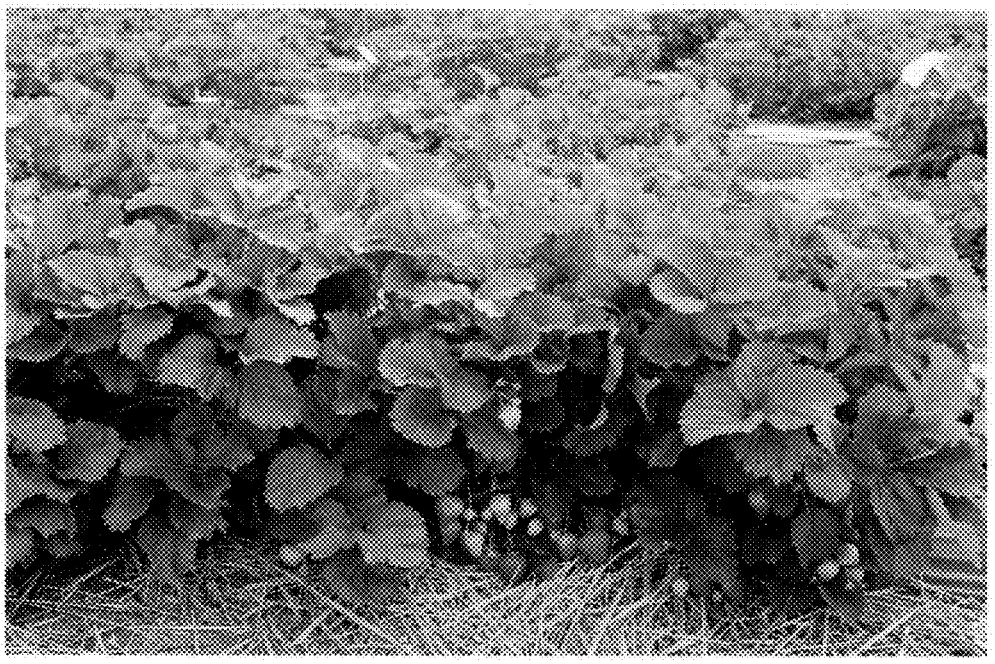
FIG. 3 shows overall plant habit including fruit at various stages of development.

The following detailed descriptions set forth the distinctive characteristics of 'Cristina'. The data which define these characteristics is based on observations taken in Ancona, Italy in 2009-2012. 'Cristina' was evaluated on non-fumigated soil having the following characteristics: pH 7.9, active calcium 9%, and texture composed at 40% clay, 25% sand and 35% silt. This description is in accordance with UPOV terminology. Color designations, color descriptions, and other phenotypical descriptions may deviate from the stated values and descriptions depending upon variation in environmental, seasonal, climatic, and cultural conditions. 'Cristina' has not been observed under all possible environmental conditions. The botanical description of 'Cristina' was taken from ten-month-old plants. Color references are primarily to The R.H.S. Colour Chart of The Royal Horticultural Society of London (R.H.S.) and to CIELAB, which is an international color system known as 'Commission Intenationale De L'Eclairage', 1978. Descriptive terminology follows the *Plant Identification Terminology, An Illustrated Glossary, 2nd* edition by James G. Harris and Melinda Woolf Harris, unless where otherwise defined.

DETAILED BOTANICAL DESCRIPTION OF THE PLANT

Classification:
- *Family*.—Rosaceae.
- *Species*.—*Fragaria×ananassa*.
- *Common name*.—Strawberry.
- *Denomination*.—'Cristina'.

Parentage:
- *Female parent*.—'CN95,602,8' (unpatented, selection of National Breeding Programme Strawberry Project — Italy).
- *Male parent*.—'CN95,419,4' (unpatented, selection of National Breeding Programme Strawberry Project — Italy).

Plant:
- *Growth habit*.—Semi-upright.
- *Height*.—41.9 cm.
- *Diameter*.—35.5 cm.
- *Number of crowns/plant*.—3.9.

Terminal leaflets:
- *Size*.—Length: 10.0 cm. Width: 9.8 cm. Length/width ratio: 1.02.
- *Number of teeth/terminal leaflet*.—73.8.
- *Shape of teeth*.—Rounded.
- *Color*.—Upper surface: CIELAB L* 37.65, a*-13.91, b* 22.23. Lower surface: CIELAB L* 52.42, a*-11.17, b* 20.37.
- *Shape in cross section*.—Concave.
- *Blistering*.—Medium.
- *Glossiness*.—Medium.
- *Number of leaflets*.—3.3.
- *Base shape*.—Obtuse.
- *Apex descriptor*.—Rounded.
- *Pubescence density*.—Moderate.
- *Margin*.—Serrate to crenate.
- *Venation pattern*.—Pinnate. Color: Upper surface: RHS 149C. Lower surface: RHS 149D.

Petiole:
- *Length*.—29.2 cm.
- *Diameter*.—0.39 cm.
- *Pubescence density*.—Moderate.
- *Pose of hairs*.—Upwards.
- *Color*.—RHS 149C.

Petiolule:
- *Length*.—2.74 cm.
- *Diameter*.—0.19 cm.
- *Color*.—RHS 149C.

Stipule:
- *Length*.—3.01 cm.
- *Width*.—0.75 cm.
- *Texture*.—Medium.
- *Anthocyanin coloration*.—RHS 52C.
- *Color*.—RHS 150C.

Stolon:
- *Diameter at bract*.—0.20 cm.
- *Avg. number of daughter plants*.—33.
- *Anthocyanin coloration*.—RHS 41B.
- *Thickness*.—Medium.
- *Pubescence*.—Medium.

Inflorescence:
- *Position relative to foliage*.—Beneath.
- *Time of flowering* (50% *of plants at first flower*).—March 30.
- *Corolla*.—Shape: Rounded. Length: 3.35 cm. Width: 3.47 cm.
- *Petals*.—Shape: Elliptic. Apex: Truncate to slightly obtuse. Base: Attenuate. Margin: Entire. Spacing: Touching. Length: 1.35 cm. Width: 3.03 cm. Length/width ratio: 0.44. Color of upper side: RHS 155C.
- *Calyx*.—Diameter: 3.88 cm. Diameter relative to corolla: Smaller. Inner calyx diameter relative to outer: Same size.
- *Sepal*.—Margin: Entire, some are jagged. Length: 1.32 cm. Width: 0.42 cm. Typical and observed sepal number per flower: 12.9. Color: RHS 144C.
- *Peduncle*.—Length: 13.94 cm. Diameter: 0.32 cm. Color: RHS 149D.

Fruit:
- *Size*.—Very large.
- *Length*.—4.44 cm.
- *Width*.—3.72 cm.
- *Length/width ratio*.—1.19 (Longer than broad).
- *Fruit hollow center* (*cavity*).—Medium.
- *Weight* (*per individual berry*).—33.7 g.
- *Predominant fruit shape*.—Conical.
- *Difference in shape between primary and secondary fruits*.—Primary fruits are very much larger than secondary fruits.
- *Fruit skin color*.—RHS 30A.
- *Evenness of fruit color*.—Even or very slightly uneven.
- *Fruit glossiness*.—Medium to strong.
- *Attitude of calyx segments*.—Downwards, some outwards.
- *Achenes*.—Insertion of achenes: Level with surface. Color: Yellow. Width of band without achenes: Absent or very narrow.
- *Firmness of flesh* (*when fully ripe*).—Firm; 328 g (as detected by penetrometer with 6 mm probe).
- *Firmness of skin*.—Medium.
- *Internal color*.—RHS 32D.
- *Sweetness*.—Medium high; 7.1° Brix.
- *Acidity*.—Medium; 10.8 meq NaOH/100 g.
- *Type of bearing*.—Not remontant; June-bearing.
- *Grams of fruit/plant*.—1213.0 g.
- *Time of ripening* (50% *of plants with first ripe fruit*).—Very late; May 21.
- *Yield*.—Medium high.

Disease, pest, and stress resistance: Not available.

COMPARISON WITH PARENTAL AND COMMERCIAL VARIETIES

When 'Cristina' is compared to the female parent 'CN95,602,8' (unpatented, selection of National Breeding Programme Strawberry Project—Italy), 'Cristina' has higher productivity, larger fruit size and later production, whereas 'CN95,602,8' has lower productivity, smaller fruit size and earlier production.

When 'Cristina' is compared to the male parent 'CN95, 419,4' (unpatented, selection of National Breeding Programme Strawberry Project—Italy), 'Cristina' has higher productivity, larger fruit size and higher fruit firmness, whereas 'CN95,419,4' has lower productivity, smaller fruit size and lower fruit firmness.

When 'Cristina' is compared to the commercial variety 'Sonata' (U.S. Plant Pat. No. 18,000), 'Cristina' has higher productivity, larger fruit size and later production, whereas 'Sonata' has lower productivity, smaller fruit size and earlier production.

We claim:

1. A new and distinct variety of strawberry plant named 'Cristina' as described and shown herein.

* * * * *